United States Patent
Brown et al.

(10) Patent No.: US 9,717,543 B2
(45) Date of Patent: Aug. 1, 2017

(54) METHODS AND IMPLANTS FOR TREATING HAMMERTOE AND OTHER DEFORMITIES

(71) Applicant: Arrowhead Medical Device Technologies LLC, Collierville, TN (US)

(72) Inventors: B. Cory Brown, Albany, TX (US); Thomas J. Twardzik, Germantown, TN (US)

(73) Assignee: Arrowhead Medical Device Technologies, LLC, Collierville, TN (US)

( * ) Notice: Subject to any disclaimer, the term of this patent is extended or adjusted under 35 U.S.C. 154(b) by 78 days.

(21) Appl. No.: 14/206,281

(22) Filed: Mar. 12, 2014

(65) Prior Publication Data
US 2014/0276825 A1    Sep. 18, 2014

Related U.S. Application Data

(60) Provisional application No. 61/780,418, filed on Mar. 13, 2013.

(51) Int. Cl.
*A61B 17/72*    (2006.01)
*A61B 17/88*    (2006.01)

(52) U.S. Cl.
CPC .......... *A61B 17/7291* (2013.01); *A61B 17/72* (2013.01); *A61B 17/88* (2013.01)

(58) Field of Classification Search
CPC ................................................. A61B 17/7291
See application file for complete search history.

(56) References Cited

U.S. PATENT DOCUMENTS 3,593,342 A    7/1971 Niebauer et al.
3,646,615 A    3/1972 Ness
(Continued)

FOREIGN PATENT DOCUMENTS

DE    19813914    9/1999
DE    20212359    11/2002
(Continued)

OTHER PUBLICATIONS

Wikipedia, Feb. 2012, "Epiphysis", https://en.wikipedia.org/w/index.php?title=Epiphysis&oldid=476635519 (last visited Jul. 12, 2016).*

(Continued)

*Primary Examiner* — Nicholas Plionis
(74) *Attorney, Agent, or Firm* — Heslin Rothenberg Farley & Mesiti P.C.; John W. Boger

(57) ABSTRACT

Surgical methods and fixation devices for bone fixation and stabilization on a patient include exposing at least a portion of a first phalanx and a second phalanx at a joint of a patient; creating a passage in an intramedullary canal of the first phalanx; inserting a first head portion of a fixation device along the passage in the intramedullary canal in a translating manner past the cancellous bone in the phalanx until the head portion engages the subchondral bone at a base of the first phalanx, the fixation device having an opposing second head portion extending out of the passage from the first phalanx; and introducing the second phalanx onto the second head portion so that the second head portion anchors in the second phalanx.

32 Claims, 10 Drawing Sheets

(56) References Cited

U.S. PATENT DOCUMENTS

| | | |
|---|---|---|
| 3,681,786 A | 8/1972 | Lynch |
| 4,262,665 A | 4/1981 | Roalstad et al. |
| 4,304,011 A | 12/1981 | Whelan, III |
| 4,516,569 A | 5/1985 | Evans et al. |
| 4,549,319 A | 10/1985 | Meyer |
| 4,667,663 A | 5/1987 | Miyata |
| 4,704,686 A | 11/1987 | Aldinger |
| 4,873,976 A | 10/1989 | Schreiber |
| 4,884,572 A | 12/1989 | Bays et al. |
| 4,898,186 A | 2/1990 | Ikada et al. |
| 4,976,715 A | 12/1990 | Bays et al. |
| 5,047,059 A | 9/1991 | Saffar |
| 5,053,035 A | 10/1991 | McLaren |
| 5,171,284 A | 12/1992 | Branemark |
| 5,201,735 A | 4/1993 | Chapman et al. |
| 5,203,864 A | 4/1993 | Phillips |
| 5,236,431 A | 8/1993 | Gogolewski et al. |
| 5,391,181 A | 2/1995 | Johnson et al. |
| 5,425,777 A | 6/1995 | Sarkisian et al. |
| 5,474,557 A | 12/1995 | Mai |
| 5,480,447 A | 1/1996 | Skiba |
| 5,667,510 A | 9/1997 | Combs |
| 5,669,912 A | 9/1997 | Spetzler |
| 5,824,095 A | 10/1998 | Di Maio, Jr. et al. |
| 5,893,850 A | 4/1999 | Cachia |
| 5,919,193 A | 7/1999 | Slavitt |
| 5,984,971 A | 11/1999 | Faccioli et al. |
| 5,993,475 A | 11/1999 | Lin et al. |
| 6,319,284 B1 | 11/2001 | Rushdy et al. |
| 6,352,560 B1 | 3/2002 | Poeschmann et al. |
| 6,689,169 B2 | 2/2004 | Harris |
| 6,692,499 B2 | 2/2004 | Tormala et al. |
| 6,736,818 B2 | 5/2004 | Perren et al. |
| 6,811,568 B2 | 11/2004 | Minamikawa |
| 7,025,789 B2 | 4/2006 | Chow et al. |
| 7,041,106 B1 | 5/2006 | Carver et al. |
| 7,918,879 B2 | 4/2011 | Yeung et al. |
| 8,100,983 B2 | 1/2012 | Schulte |
| 8,202,306 B2 | 6/2012 | Dreyfuss |
| 8,337,537 B2 | 12/2012 | Pelo et al. |
| 8,475,456 B2 | 7/2013 | Augoyard et al. |
| 2002/0082705 A1 | 6/2002 | Bouman et al. |
| 2004/0220574 A1 | 11/2004 | Pelo et al. |
| 2006/0129153 A1 | 6/2006 | Klaue et al. |
| 2007/0243225 A1 | 10/2007 | McKay |
| 2008/0177262 A1 | 7/2008 | Augoyard et al. |
| 2008/0195219 A1 | 8/2008 | Wiley et al. |
| 2008/0221697 A1 | 9/2008 | Graser |
| 2009/0036893 A1 | 2/2009 | Kartalian et al. |
| 2010/0076503 A1* | 3/2010 | Beyar ............... A61B 17/1615 606/86 R |
| 2010/0312244 A1* | 12/2010 | Edwards ............ A61B 17/1725 606/62 |
| 2010/0324556 A1 | 12/2010 | Tyber et al. |
| 2011/0004255 A1 | 1/2011 | Weiner et al. |
| 2011/0118739 A1 | 5/2011 | Tyber et al. |
| 2011/0144644 A1 | 6/2011 | Prandi et al. |
| 2011/0172668 A1 | 7/2011 | Frake |
| 2011/0257652 A1 | 10/2011 | Roman |
| 2011/0257755 A1 | 10/2011 | Bellemere et al. |
| 2011/0301652 A1 | 12/2011 | Reed et al. |
| 2012/0089197 A1 | 4/2012 | Anderson |
| 2012/0197254 A1* | 8/2012 | Wolfe ............... A61B 17/1717 606/62 |
| 2013/0165982 A1* | 6/2013 | Ek ........................ A61B 17/84 606/328 |
| 2013/0172889 A1 | 7/2013 | Tyber et al. |
| 2014/0277191 A1* | 9/2014 | Evans ............... A61B 17/7225 606/308 |

FOREIGN PATENT DOCUMENTS

| | | |
|---|---|---|
| DE | 10134511 | 2/2003 |
| DE | 20218993 | 2/2003 |
| EP | 1870050 | 12/2007 |
| FR | 2846545 | 5/2004 |
| GB | 2430625 | 4/2007 |
| WO | WO-2005063149 | 7/2005 |
| WO | WO-2006099886 | 9/2006 |
| WO | WO 2011130229 | 10/2011 |

OTHER PUBLICATIONS

Integra™ "IPP-ON™ Interphalangeal Implant" 2008, 6 pages.
Supplementary European Search Report issued for EP 11769413 dated May 6, 2014, 6 pages.
International Search Report and Written Opinion issued for PCT/US2014/022058, dated Jun. 25, 2014, 15 pages.
International Search Report and Written Opinion issued for PCT/US2014/0244858, dated Jul. 10, 2014, 17 pages.
International Search Report and Written Opinion issued for PCT/US2014/024599, dated Aug. 6, 2014, 11 pages.
International Searching Authority/United States Patent Office, "International Search Report" for PCT/US2011/032057, mailed Jul. 5, 2011, 2 pages.
SmartToe Intramedullary Shape memory Implant, product information, Memometal, Inc., 2009, 2 pages.
SmartToe Intramedullary Memory Implant, "Old Standard versus the Gold Standard" promotion, MMI-USA, Memphis, TN, 1 page.
PRO-TOE™ VO hammertoe Fixation System, Surgical Technique, FA196-410R311, Wright Medical Technology, Inc., 2011, 12 pages.
PRO-TOE™ Hammertoe Implant System, Alpha Surgical Technique for the PRO-TOE VO Implant, Wright Medical Technology, Inc., Rev. 10.10, 6 pages.
Crenshaw, A. H., ed., "Campbell's Operative Orthopaedics, vol. 2," 7th edition, The C.V. Mosby Company, Washington DC, 1987, p. 937-945, cover and copyright pages, 11 pages.

* cited by examiner

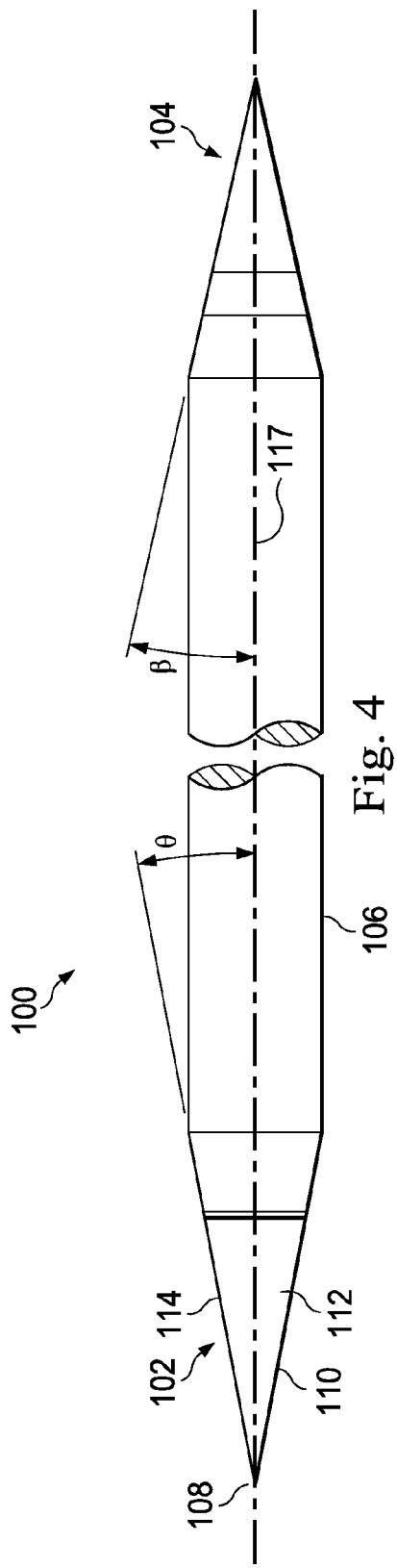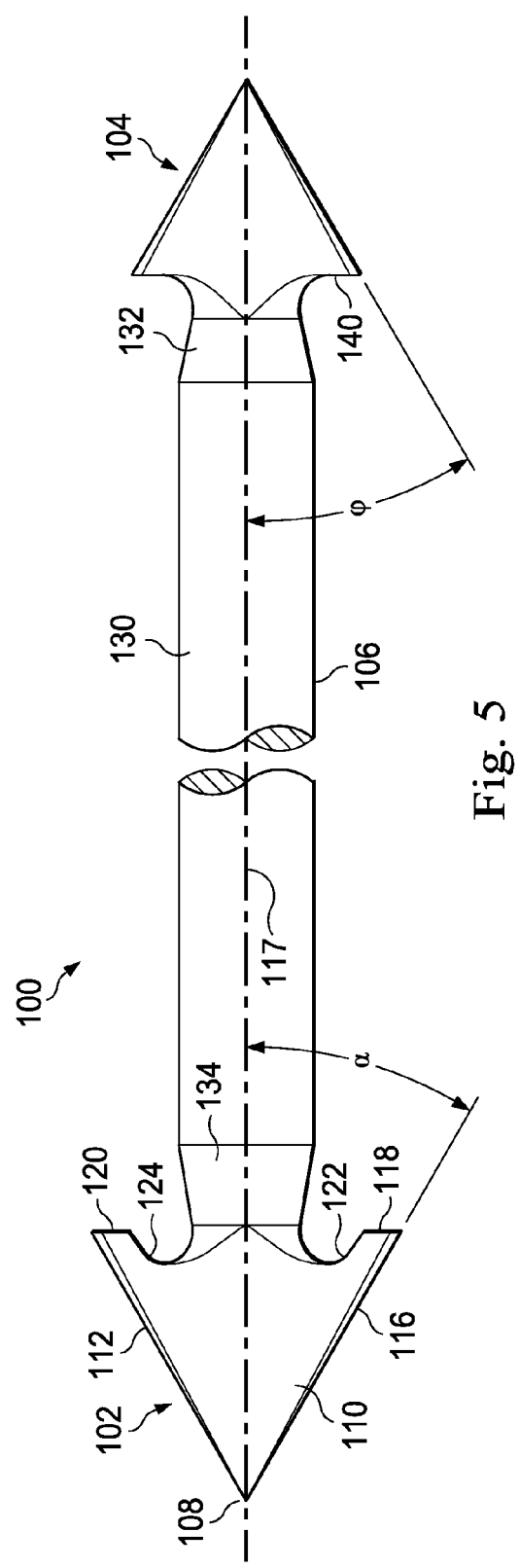

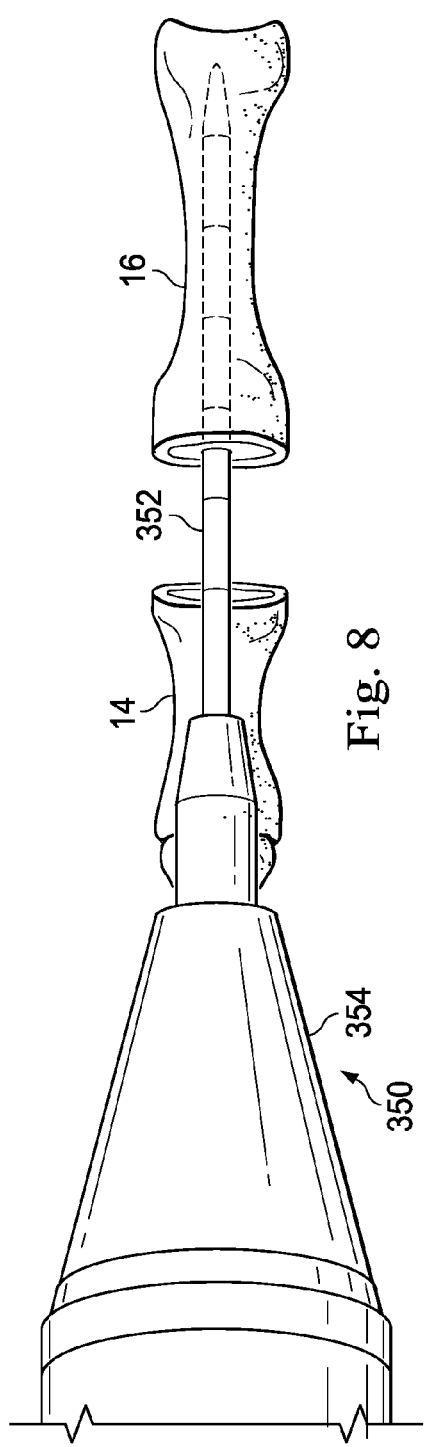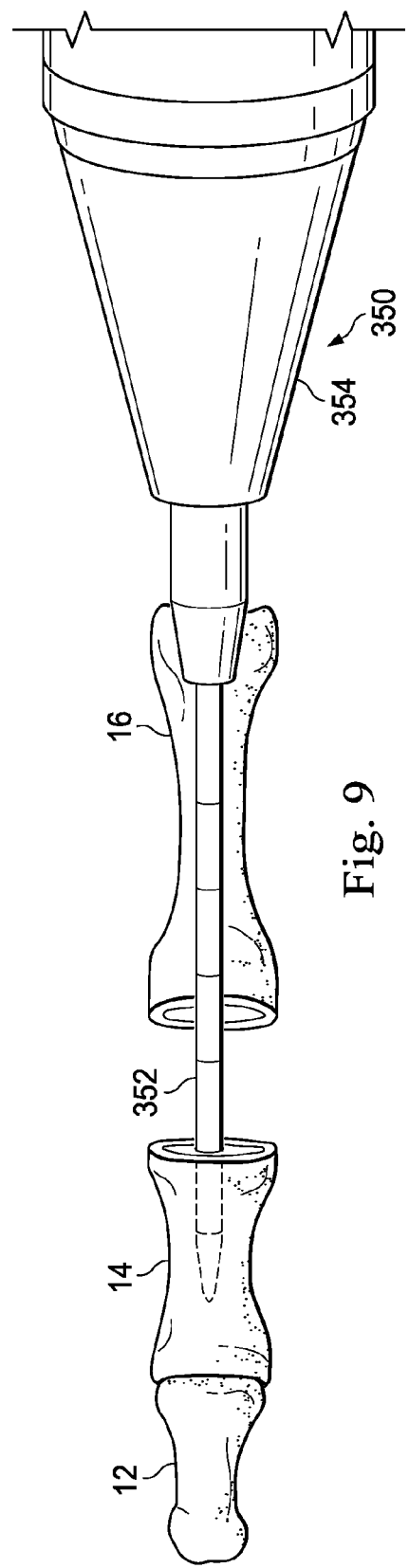
Fig. 8
Fig. 9

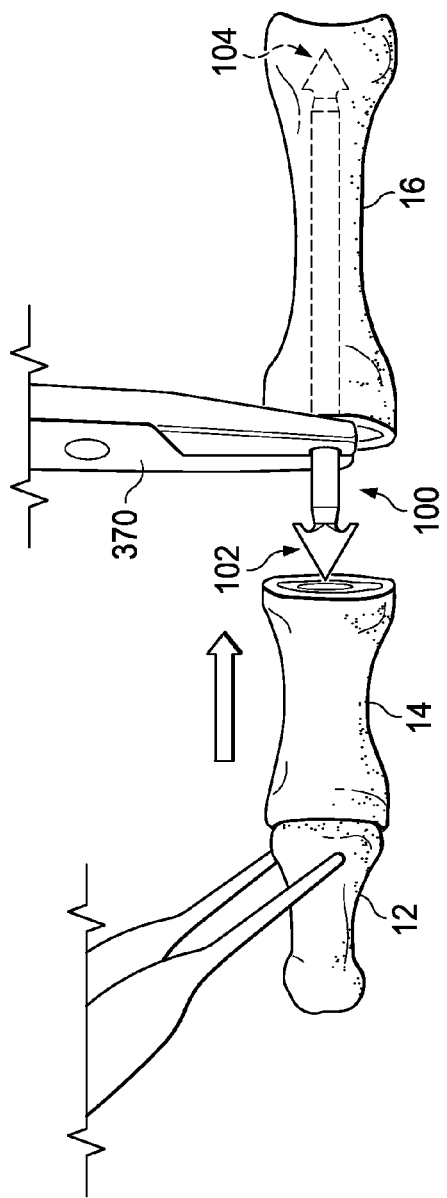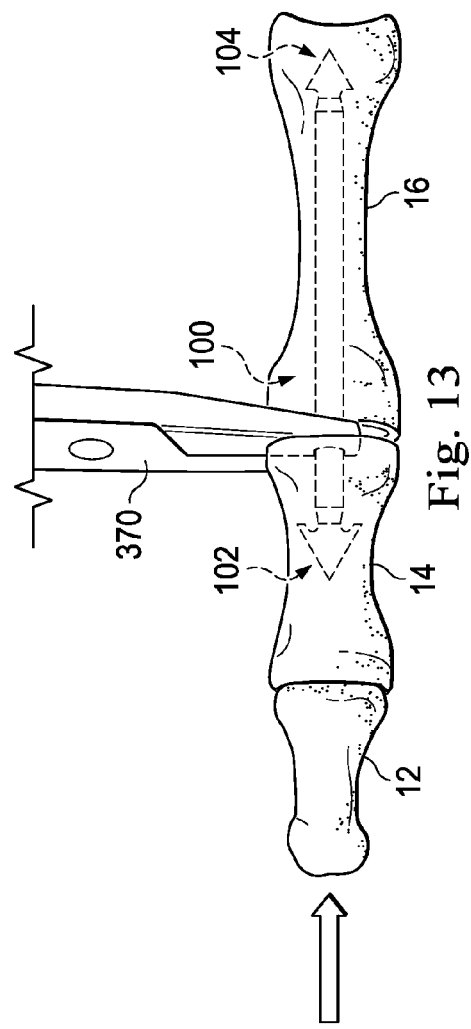

METHODS AND IMPLANTS FOR TREATING HAMMERTOE AND OTHER DEFORMITIES

PRIORITY DATA

This application claims priority to Provisional Patent Application No. 61/780,418, filed Mar. 13, 2013, and entitled "Methods and Implants for Treating Hammertoe and Other Deformities," the disclosure of which is hereby incorporated by reference in its entirety.

BACKGROUND

Hammertoe deformities occur when the metatarsophalangeal joint between phalanges in a toe are cocked upward and the proximal interphalangeal joint bends downward. This deformity can become quite painful and can limit the ability of a person with hammertoe to walk and perform other daily activities. Hammertoe may be caused by any number of factors, including heredity, the long-term use of poorly fitting shoes, having a long second toe, hallux valgus pressing against the second toe, connective tissue disorders, and trauma.

While some minor cases may be treated with non-surgical remedies, surgeries are often necessary to provide real correction and pain relief. Some surgical methods include stabilizing the toes using a smooth K-wire placed in an antegrade manner through the middle and distal phalanges while joint extension and distraction are maintained. The K-wire may then be placed in retrograde fashion into the proximal phalanx while joint extension and distraction are maintained. Fixation lasts for 4-6 weeks after surgery. During that time, the pins are capped so that the sharp ends do not catch on objects, such as bed sheets. Even with this form of fixation, non-unions, K-wire migration, and loss of fixation can be quite common. Further, the external K-wires may lead to pin tract infections or movement of bone along the smooth wire, including rotation of the distal aspect of the toe. These types of challenges make alternative fixation methods desirable.

The methods and implant devices disclosed herein overcome one or more of the deficiencies of the prior art.

SUMMARY

In accordance with an exemplary aspect, the present disclosure is directed to a surgical technique for bone fixation and stabilization on a patient. The technique includes exposing at least a portion of a first phalanx and a second phalanx at a joint of a patient; creating a passage in an intramedullary canal of the first phalanx; and inserting a first head portion of a fixation device along the passage in the intramedullary canal in a translating manner past the cancellous bone in the phalanx until the first head portion engages subchondral bone at a base of the first phalanx. The fixation device may have an opposing second head portion extending out of the passage from the first phalanx. The technique also includes introducing the second phalanx onto the second head portion so that the second head portion anchors in the second phalanx.

In an aspect, the technique includes inserting more than 60% of the fixation device into the intramedullary canal of the first phalanx. In an aspect, the fixation device has a longitudinal length, and the method comprises grasping the fixation device with an insertion instrument at a location more than 60% of the longitudinal length from the first head portion in order to insert the first head portion along the passage and to engage the subchondral bone. In an aspect, inserting the first head portion in a translating manner includes rotating the fixation device less than about 45 degrees during insertion. In an aspect, the first head portion comprises trailing edge surfaces configured to anchor in the subchondral bone. In an aspect, the first head portion has a diameter less than 2.5 mm. In an aspect, the technique includes measuring the size of the intramedullary canal to ensure the first head portion can pass therethrough. In an aspect, the technique includes intraoperatively trimming the first head portion to decrease its diameter when the first head portion is too large to pass through the intramedullary canal. In an aspect, the first head portion has a smaller diameter than the second head portion. In an aspect, the first head portion is a proximal head portion and the second head portion is distal head portion, and wherein the first phalanx is a proximal phalanx and the second phalanx is an intermediate phalanx. In an aspect, introducing the second phalanx onto the second head portion includes advancing the second head portion past cancellous bone in the second phalanx until the second head portion engages subchondral bone in the second phalanx.

In accordance with an exemplary aspect, the present disclosure is directed to a surgical technique for bone fixation and stabilization on a patient. The technique includes exposing at least a portion of a first phalanx and a second phalanx at a joint of a patient, the first phalanx being more proximal than the second phalanx; creating a passage in an intramedullary canal of the first phalanx; inserting more than 60% of a fixation device into the passage in the intramedullary canal past the cancellous bone in the phalanx until a first head portion of the fixation device engages the subchondral bone at a base of the first phalanx. The fixation device has an opposing second head portion extending out of the passage from the first phalanx, and the technique also includes introducing the second phalanx onto the second head portion so that the second head portion anchors in the second phalanx.

In an aspect, inserting comprises translating the fixation device along the passage so that the device rotates less than about 45 degrees while inserting. In an aspect, the fixation device has a longitudinal length, and the method comprises grasping the fixation device with an insertion instrument at a location more than 60% of the longitudinal length from the first head portion in order to insert more than 60% of the fixation device into the first phalanx to engage the subchondral bone. In an aspect, the first head portion comprises trailing edge surfaces configured to anchor in the subchondral bone. In an aspect, wherein the first head portion has a diameter less than 2.5 mm. In an aspect, the technique includes measuring the size of the intramedullary canal to ensure the first head portion can pass therethrough.

In an aspect, the present disclosure is directed to an intramedullary fixation device used in bone fixation and stabilization on a patient. The fixation device includes a longitudinally extending rigid body having a rigidity sufficient to withstand bending loading applied by the phalanges; a distal head disposed at a distal end of the body and sized for insertion into an intramedullary canal of a first phalanx of the patient, the distal head having a diameter greater than 2.5 mm and being configured to anchor in cancellous bone of the first phalanx of the patient; and a proximal head disposed at a proximal end of the body and sized for insertion into an intramedullary canal of a second phalanx of the patient, the proximal head having a diameter of about 2.5 mm or smaller, the proximal head being configured to anchor in subchondral bone of the second phalanx of the patient.

In an aspect, the distal head and the proximal head each have anchors formed therein for anchoring in the respective cancellous bone and subchondral bone. In an aspect, the distal head comprises anchors formed of trailing surfaces forming barbs and the proximal head comprises trailing surfaces substantially normal to a longitudinal axis of the body.

In accordance with an exemplary aspect, the present disclosure is directed to a surgical technique for bone fixation and stabilization on a patient, comprising: exposing a proximal interphalangeal joint (PIPJ) joining a proximal phalanx and an intermediate phalanx, and a distal interphalangeal joint (DIPJ) joining a the intermediate phalanx and a distal phalanx; creating a hole entirely through the intermediate phalanx; creating a hole into the proximal phalanx; inserting a first head portion of a fixation device through the hole in the intermediate phalanx and into the hole in the proximal phalanx so that an opposing second end of the fixation device extends out of the passage from the intermediate phalanx; and introducing the distal phalanx onto the second head portion so that the second head portion anchors in the distal phalanx.

In an aspect, creating a hole into the proximal phalanx includes creating a hole extending through the cancellous bone and to the subchondral bone at a proximal base of the proximal phalanx. In an aspect, inserting the first head portion into the hole in the proximal phalanx includes advancing the first head portion through the cancellous bone until it engages the subchondral bone at a proximal base of the proximal phalanx. In an aspect, the surgical technique includes inserting more than 60% of the fixation device into the intramedullary canal of the intermediate and proximal phalanges. In an aspect, the fixation device has a longitudinal length, and the method comprises grasping the fixation device with an insertion instrument at a location more than 60% of the longitudinal length from the first head portion in order to insert the first head portion along the passage and engage subchondral bone of the proximal phalanx. In an aspect, inserting the first head portion includes advancing the head portion in a translating manner. In an aspect, the translating manner includes rotating the device within the hole in less than about 45 degrees while advancing the head portion. In an aspect, the first head portion has a diameter less than 2.5 mm. In an aspect, the surgical technique includes measuring the size of the intramedullary canal of the intermediate and proximal phalanges to ensure the first head portion can pass therethrough. In an aspect, the first head portion has a smaller diameter than the second head portion. In an aspect, the surgical technique includes grasping the fixation device with a surgical instrument between the proximal phalanx and the intermediate phalanx while introducing the distal phalanx onto the second head portion. In an aspect, introducing the second phalanx onto the second head portion includes advancing the second head portion past cancellous bone in the second phalanx until the second head portion engages subchondral bone in the second phalanx.

In an exemplary aspect, the present disclosure is directed to a surgical technique for bone fixation and stabilization on a patient. The technique may include exposing a proximal interphalangeal joint (PIPJ) joining a first phalanx and a second phalanx, and a distal interphalangeal joint (DIPJ) joining the second phalanx and a third phalanx; inserting a first head portion of a fixation device entirely through the second phalanx and into the first phalanx until the first head portion engages subchondral bone in a proximal base of the first phalanx, and so that an opposing second end of the fixation device extends out of the passage from the second phalanx; and introducing the third phalanx onto the second head portion so that the second head portion anchors in the third phalanx.

In an aspect, the surgical technique may include forming a pilot hole from the DIPJ entirely through the second phalanx; forming a pilot hole from the DIPJ through the first phalanx until the pilot hole reaches subchondral bone; and forming a pilot hole from the DIPJ through a portion of the third phalanx. In an aspect, inserting the first head portion includes advancing the head portion in a translating manner. In an aspect, the translating manner includes rotating the device within the hole in less than about 45 degrees during insertion. In an aspect, the first head portion has a diameter less than 2.5 mm.

In an aspect, the present disclosure is directed to an intramedullary fixation device used in bone fixation and stabilization on a patient. The fixation device may include a longitudinally extending rigid body having a rigidity sufficient to withstand bending loading applied by phalanges of the patient, the rigid body having a length sufficient to span two adjacent joints formed between adjacent phalanges; a distal head disposed at a distal end of the body and sized for insertion into an intramedullary canal of a first phalanx of the patient, the distal head having a diameter greater than 2.5 mm and being configured to anchor in cancellous bone of the first phalanx of the patient; and a proximal head disposed at a proximal end of the body and sized for insertion into an intramedullary canal of a second phalanx of the patient, the proximal head having a diameter of about 2.5 mm or smaller, the proximal head being configured to anchor in subchondral bone of the second phalanx of the patient.

In an aspect, the distal head and the proximal head each have pyramidal shaped arrows for advancing into the phalanges and each have anchors formed therein for anchoring in the respective cancellous bone and subchondral bone. In an aspect, the distal head comprises anchors formed of barbs and the proximal head comprises anchors formed of trailing surfaces substantially normal to a longitudinal axis of the body.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 4 is an illustration of an exemplary intramedullary fixation device in accordance with one aspect of the present disclosure.

FIG. 5 is an illustration of the exemplary intramedullary fixation device of FIG. 4 in accordance with one aspect of the present disclosure.

FIG. 8 is an illustration of phalanges undergoing a surgical technique in accordance with one aspect of the present disclosure.

FIG. 9 is an illustration of phalanges undergoing a surgical technique in accordance with one aspect of the present disclosure.

FIG. 12 is an illustration of phalanges undergoing a surgical technique in accordance with one aspect of the present disclosure.

FIG. 13 is an illustration of phalanges undergoing a surgical technique in accordance with one aspect of the present disclosure.

DETAILED DESCRIPTION

Figure 1:
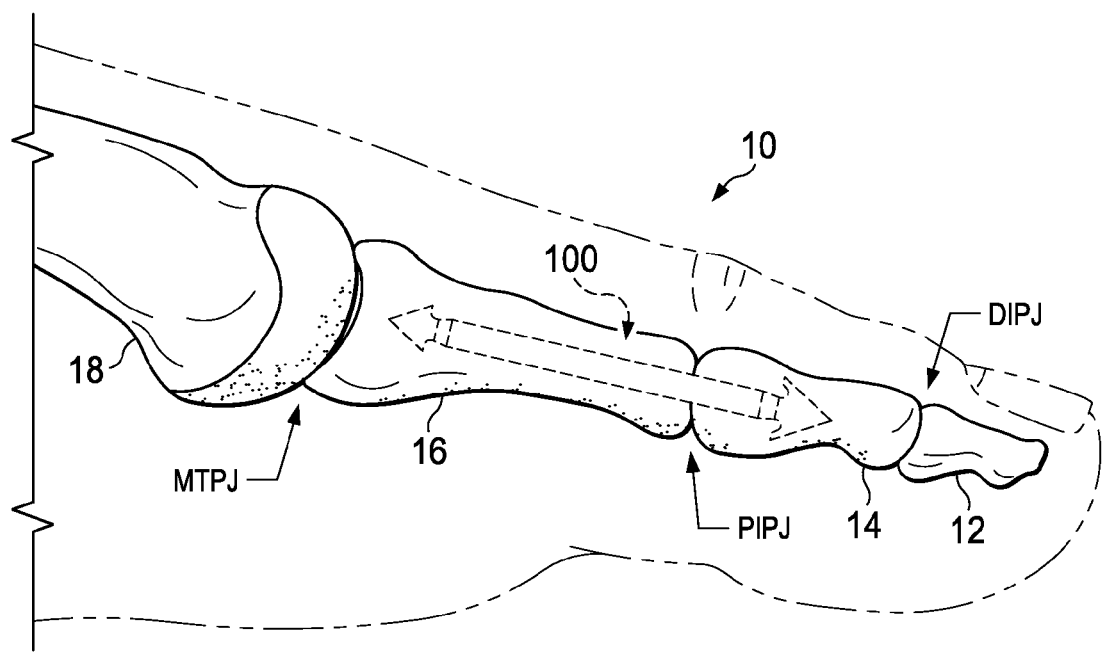
FIG. 1 is an illustration of an exemplary intramedullary fixation device disposed between and within adjacent phalanges of a toe of a patient in accordance with one aspect of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to techniques and intramedullary implants for bone fixation and stabilization of toes and fingers across fusion or fracture sites, and treats deformities, including for example, hammertoe deformities. In an exemplary aspect, the techniques include anchoring a fixation device deeply in a proximal phalanx so that the fixation device anchors in the subchondral bone. Anchoring in the subchondral bone may provide a stronger pull-out resistance and may enable reduction of the overall diameter of the fixation device, while also providing additional support to the phalanx. In another exemplary aspect, the techniques include spanning both a distal interphalangeal joint and a proximal interphalangeal joint with a single fixation device in order to increase the stability of the fixation device in the treated phalanges and provide continuity to the injured or deformed digit.

FIG. 1 shows an exemplary toe 10 having a distal phalanx 12, a distal interphalangeal joint (DIPJ), an intermediate phalanx 14, a proximal interphalangeal joint (PIPJ), a proximal phalanx 16, and a metatarsal bone 18. A metatarsophalangeal joint (MTPJ) joins the metatarsal bone and the proximal phalanx 16, a proximal interphalangeal joint (PIPJ) joins the proximal phalanx 16 and the intermediate phalanx 14, and a distal interphalangeal joint (DIPJ) joins the intermediate phalanx 14 and the distal phalanx 12. In this example, the toe 10 has been surgically treated to correct a deformity such as hammertoe as discussed above. Accordingly, the toe 10 includes an implanted intramedullary fixation device 100 disposed therein in accordance with an exemplary aspect of the present disclosure. In this example, the fixation device 100 fuses the PIPJ by extending between and being implanted within the intermediate and proximal phalanges 14 and 16.

Figure 2:
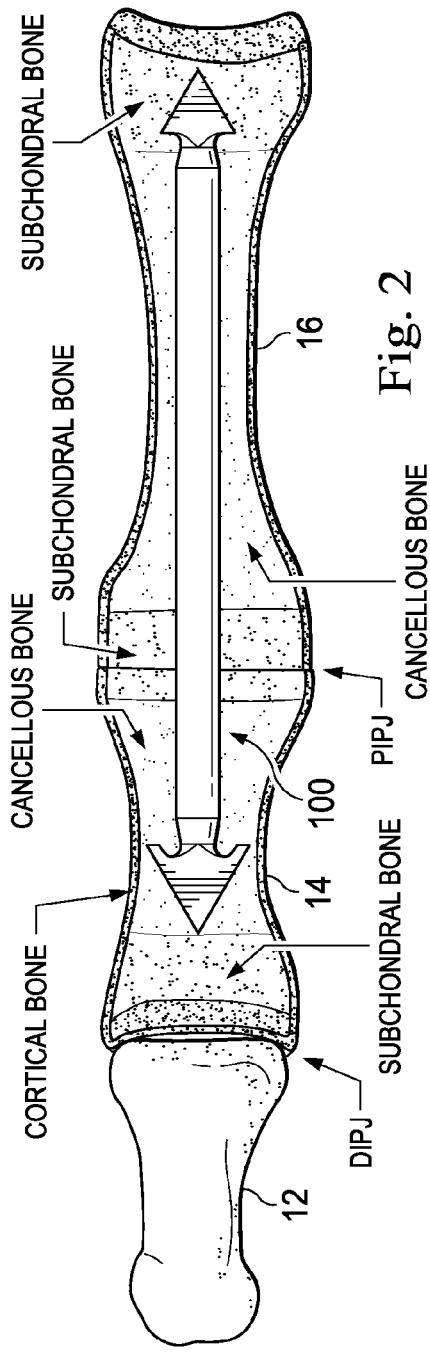
FIG. 2 is an illustration of an exemplary intramedullary fixation device disposed between and within adjacent phalanges of a toe of a patient in accordance with an exemplary aspect of the present disclosure.

FIG. 2 shows the exemplary fixation device 100 having a portion anchored in the subchondral bone of the proximal phalanx 16 and a portion anchored in the intermediate phalanx 14, thereby fusing the PIPJ. The techniques and systems disclosed herein enable the device 100 to be suitably anchored with increased pull-out force by anchoring in the more dense subchondral bone of the proximal phalanx 16 instead of the less dense cancellous bone of the phalanges or by pressing against opposite cortical walls of the phalanges.

Figure 3:
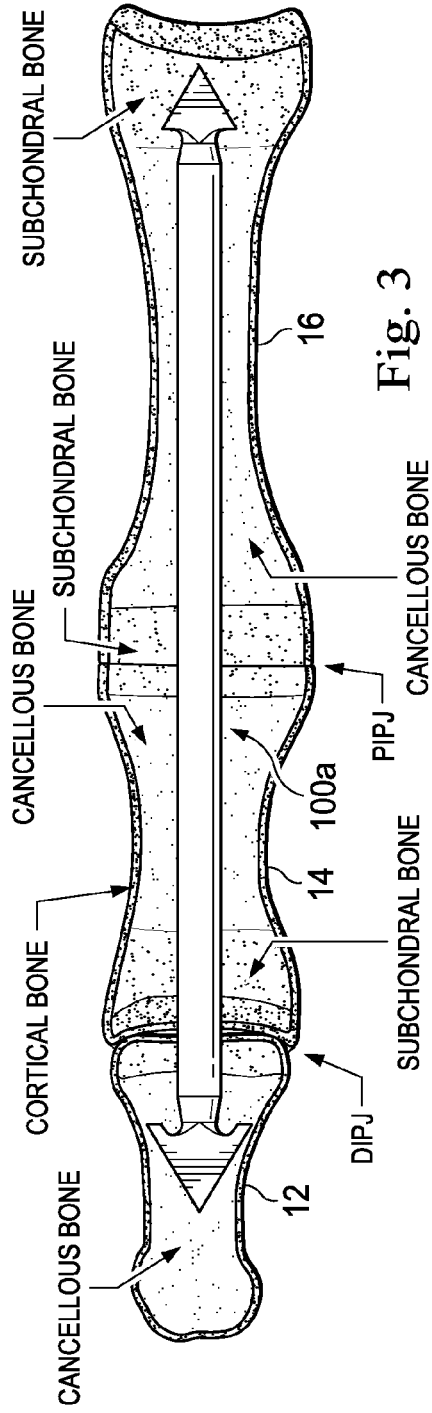
FIG. 3 is an illustration of an exemplary intramedullary fixation device disposed between and within adjacent phalanges of a toe of a patient in accordance with an exemplary aspect of the present disclosure.

FIG. 3 shows an exemplary device 100a anchored in the subchondral bone of the proximal phalanx 16, entirely passing through the intermediate phalanx 14, and anchored in the distal phalanx 12. Accordingly, in this embodiment, the device 100a is formed to span more than a single joint, providing a more unified rigid support to the patient and also potentially having efficiencies in surgery in instances where multiple joint fixation is required. Here, the fixation device 100a fuses both the PIPJ and the DIPJ.

Referring to FIGS. 2 and 3, the phalanges are formed with more dense subchondral bone at the bases and crowns of the phalanges adjacent the joints, and with less dense cancellous bone filling the medullary cavity between the bases of the phalanges. The subchondral bone in the lesser toes is the layer of bone just below the cartilage the density of which gradually decreases as the bone changes to spongy cancellous bone. The subchondral bone can extend up to 12 mm from the base or crown of the phalanx before becoming completely cancellous bone depending on the patient's anatomy and quality of bone. In some aspects, the fixation devices herein achieve fixation from 1 mm to 10 mm from the base or crown of the phalanx. The intramedullary canal extends between one region of the subchondral bone to the other. Cortical bone forms the surface of each phalanx. Conventional systems attempt to anchor implant devices for treating hammertoe by introducing the implant along the intramedullary canal a short distance into the phalanx to engage the cortex and/or provide fixation in the cancellous bone. To provide suitable anchoring, these conventional implants typically have anchoring heads or diameters exceeding 2.5 mm and typically in the range of 3.0-4.0 mm. These large heads are intended to have a sufficient area or diameter to engage the cortical bone to hold the device in place initially while the cancellous bone contributes incremental stability behind the large heads to resist pull-out. However, the present system may provide as much or more pullout resistance with a head diameter of 2.5 mm anchored in the subchondral bone than a device with a head diameter of 3.5 mm anchored in the cancellous bone. To accommodate this new anchoring location, the fixation device 100 has a length considerably greater than a conventional implant. Accordingly, by increasing the length of the fixation device, and reducing the size of the diameter of the head, anchoring ability is increased while at the same time, the overall phalanx support is also increased. The longer shaft can also contribute to the implant's stability by providing numerous point of contact between the intramedullary canal and the implant shaft. Furthermore, the smaller head diameter of 2.5 mm of the fixation device 100 may enable passage through even the most narrow isthmus of the intramedullary canals of the lesser toes. When treating patients with extraordinarily narrow intramedullary canals, the system 100 is configured for intra-operative trimming of the anchoring head to reduce the diameter to as little as 1.5 mm.

FIGS. 4 and 5 show one exemplary embodiment of the fixation device 100 and may also correspond to the fixation device 100a. The device 100 is designed with a three-dimensionally configured arrow at each end and includes a relatively larger distal head 102, a relatively smaller proximal head 104, and a body 106 extending between the distal and proximal heads 102, 104. As will become apparent from the below description, the individual components of the device 100 work in conjunction with one another to stabilize bone during arthrodesis procedures and across fractures. While the heads are described as proximal and distal heads, it should be understood that the proximal head may be implanted in a distal position and the distal head may be implanted in a proximal position.

The distal head 102 is formed as a three dimensional arrowhead that is sized for placement in an intramedullary canal of a patient. It is configured so that edges of the arrowhead grasp the cortical bone and/or the cancellous bone in the medullary canal as it is inserted or grasp the subchondral bone in the base of the phalanx, stabilizing the arthrodesis or fusion site during the osseous union. In this exemplary embodiment, the distal head 102 is formed as a distal end having a distal-most point 108.

First, second, third, and fourth outer facing surfaces 110, 112, 114, 116 intersect at and extend from the distal most point 108 in the proximal direction, forming a four-sided pyramidal shape. Although shown as having four outer facing surfaces, some embodiments include greater or fewer outer facing side surfaces. In the example shown, opposing surfaces angle away from each other to define a leading angle. For example, the opposing first and third outer facing surfaces 110, 114 define an angle θ relative to a longitudinal axis 117 of the arrowhead shaped distal head 102. In some examples, the angle θ is in the range of about 5 degrees to about 45 degrees. In other examples, the angle θ is in the range of about 7-20 degrees, and in some embodiments, the angle is around 11 degrees. In a similar manner, the opposing second and fourth outer facing surfaces 112, 116 of the arrowhead shaped distal head 102 form an angle α. In the example shown, the angle α is larger than the angle θ. The angle α may be selected to be within the range of about 15-60 degrees, and in some embodiments, is in the range of about 20-45 degrees. In some examples, the angle α is about 30 degrees. The multiple angles described on the distal head may vary based on the size and strength of bone in which the device is to be implanted.

In the embodiment shown, the second and fourth outer facing surfaces 112, 116 have rounded outer surfaces. At the proximal end of these surfaces, the second and fourth outer facing surfaces 112, 116 have a diameter D within a range of about, for example, 2.5-4.5 mm. In some embodiments, the diameter D is in a range of about 3.0-4.0 mm, and in one embodiment, the diameter D is about 3.5 mm. In other embodiments, the second and fourth outer facing surfaces 112, 116 are each planar surfaces.

Because of the different angles between the opposing first and third surfaces 110, 114 and the opposing second and fourth surfaces 112, 116, the width of the distal head 102 differs from side to side. This is easily seen by comparing FIGS. 3 and 4, different views of the distal head 102. This differing width increases resistance to rotation that may occur if the device 100 were cylindrical or to a lesser extent substantially square, although such embodiments are contemplated. Further, the differing width may permit an implanted fixation device to be removed, rotated 90 degrees and implanted again while still providing satisfactory anchoring.

In the example shown, the distal head 102 includes two proximally projecting barbs 118, 120. These barbs are configured to engage tissue within the intramedullary canal and resist movement and migration and/or axial displacement within the canal once they have been inserted into the canal. As can be seen, these barbs 118, 120 are formed by edges of respective outer facing surfaces 112, 116 and because of the pyramidal shape of the distal head, the edges lie in substantially parallel lines.

Inner surfaces of the barbs 118, 120 are formed by first and second undercuts 122, 124 disposed respectively between tips of the barbs 118, 120. These are described in prior U.S. patent application Ser. No. 13/084,048 to Roman, filed Apr. 11, 2011, and incorporated herein by reference.

In some embodiments, the barbs are flexible enough to bend if a hard cortical wall is engaged during insertion, providing a reduction in diameter, and enabling additional advancement into an intramedullary canal. In one embodiment, the flexing barbs invoke a change in diameter in the range of about 0.1-0.3 mm. In some examples, the barbs are designed in such a manner that one or both barbs can be trimmed intra-operatively with a straight pin cutter to reduce the diameter of the arrow to fit particularly narrow intramedullary canals. If necessary, the arrowhead tip may be completely removed.

The body 106 extends between and connects the distal head 102 and the proximal head 104. It is a one-piece rigid element structurally configured to withstand loading applied across the joint or fracture being supported. It includes a main body portion 130 and necks 132, 134 at either end leading to the distal and proximal heads 102, 104. As can be seen, the main body portion 130 has a diameter larger than that of the necks 132, 134. The larger body portion 130 may be easier to grasp and secure with a surgical instrument because it has a larger perimeter surface area, while the necks 132, 134 may be sized to permit additional tissue placement and tissue growth immediately adjacent the undercut surfaces 122, 124 of the distal and proximal heads 102, 104. This may result in more secure and lasting anchoring. Thus, this structural arrangement may provide space for extra tissue to grow behind the arrowhead to aid in fixation, while still providing a large gripping surface on the body 106.

The second or proximal head 104 is, in the example shown, smaller than the distal head 102, and extends from the body 106 in the opposing direction. For clarity and to reduce duplication, much of the description above applies to the proximal head 104 and is not repeated here with the understanding that the description above applies to the proximal head 104. As such, the proximal head includes four main surfaces forming an arrowhead. As can be seen, some of these surfaces form an angle β and others form an angle φ relative to the longitudinal axis. In one embodiment, the angle β is smaller than the angle θ. In some embodiments, the angle β ranges from about 7-25 degrees, and in one embodiment is 11 degrees. The angle φ may be within a range discussed above relative to the angle α, and in one embodiment, is equal to the angle α.

In this embodiment, the proximal head 104 is formed with trailing edge surfaces 140 instead of projecting barbs. The trailing edge surfaces 140 enable bone ingrowth immediately adjacent the trailing edge surfaces, resulting in a relatively quick purchase of the proximal head 104 during healing. The trailing edge surfaces 140 extend substantially perpendicular to the longitudinal axis 117 of the device 100.

The proximal head 104 is sized and configured to be inserted through the intramedullary canal and implanted in the subchondral bone at the base of the proximal phalanx. To do this, the proximal head has a maximum diameter (or width, referred to herein as a diameter) of 2.5 mm and has a length permitting it to be anchored within the subchondral bone. In one aspect, the diameter of the head is in the range of about 1.5-2.5 mm. In another aspect, the diameter is within a range of about 2.0-2.5 mm. As such, this proximal head 104 has a smaller diameter and length than the larger distal head 102. Because it is implanted in the more dense subchondral bone at the base of the proximal phalanx, the proximal head 104 may achieve a stability and resistance to migratory forces that is similar to that of the larger distal head 102, which is shaped and configured to be inserted in the less dense cancellous bone of the intermediate phalanx.

The fixation device 100 disclosed herein is unique in that it includes a proximal head having a maximum diameter of 2.5 mm, has an arrowhead-shaped tip, and has a length permitting it to be anchored within the subchondral bone while fusing a joint. In one aspect, the diameter of the proximal head 104 is in the range of about 1.5-2.5 mm as discussed above. Various fixation device lengths may be provided to meet patient sizing restrictions and to extend all the way to the base of the proximal phalanx to engage the subchondral bone. In one aspect, the length of the fixation device 100 in the range of about 19-80 mm. In another aspect, the length is in the range of about 23-50 mm. In yet another embodiment, the length is about 25 mm Other lengths and ranges are contemplated. The length of fixation device 100 is important because the fixation device 100 is configured to not only penetrate the subchondral bone, but to also anchor in the subchondral bone. In addition, the length of the devices enables the anchor formed of the barbs or trailing edge surfaces to not only lie within the more dense subchondral bone, but to be disposed a far distance from the site of the arthrodesis. This orientation contributes to the stability of the fixation device when fusing the individual proximal interphalangeal joint (PIPJ) and distal interphalangeal joint (DIPJ) and even more so when fusing both the PIPJ and DIPJ with a single fixation device as shown in FIG. 3. Spanning the arthrodesis site by as great a distance as possible may maximize stability of the device used in hammertoe or other fixation. Further, because the distance from the head and the site of the resection is so long, the stability of the fixation device is enhanced by the multiple points of contact of the shaft along the intramedullary canal.

Figure 6:
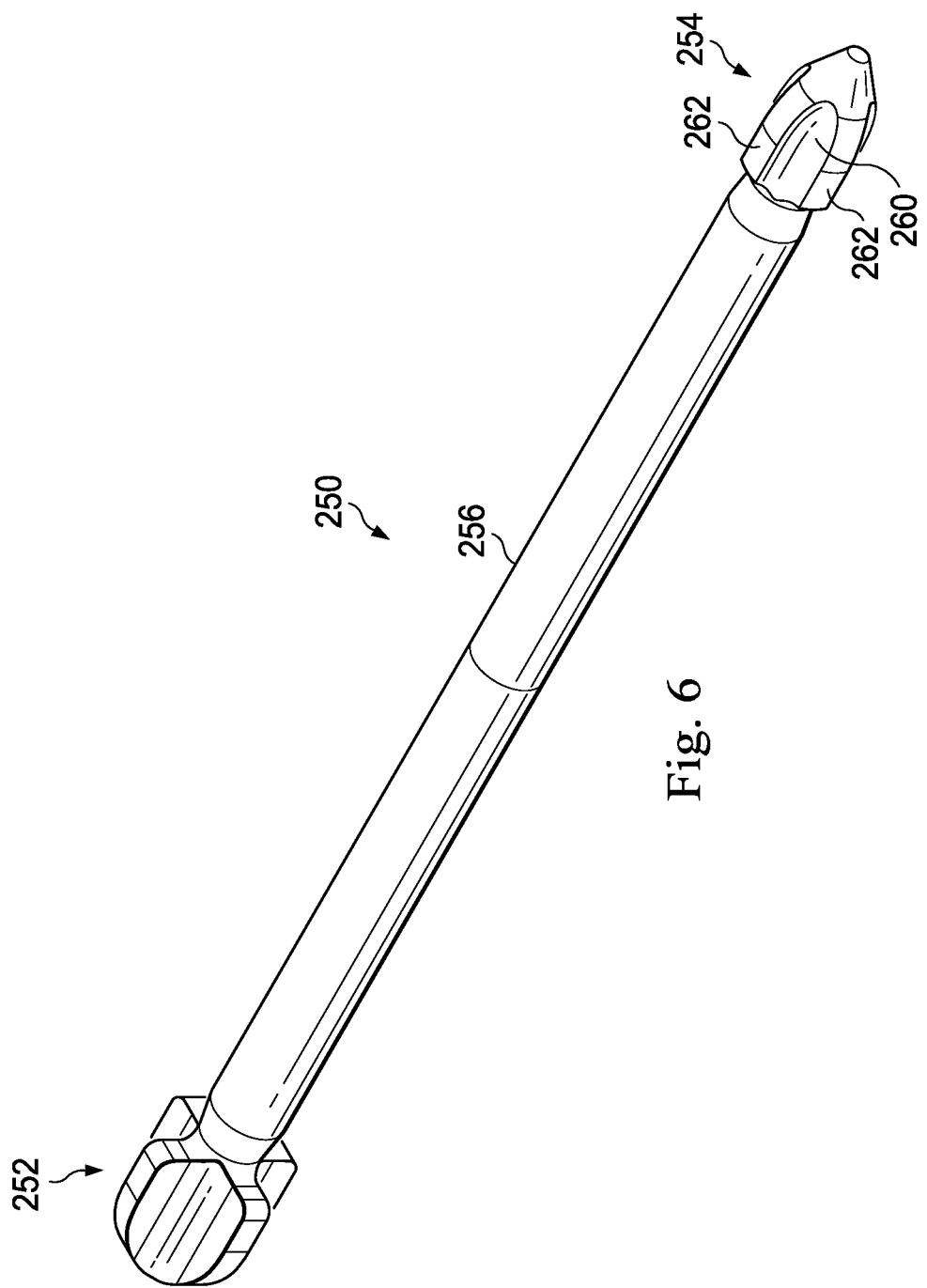
FIG. 6 is an illustration of another exemplary intramedullary fixation device in accordance with one aspect of the present disclosure.

FIG. 6 shows another exemplary embodiment of a device 250 suitable for implanting according to the principles and techniques of this disclosure. The device includes a distal head 252, a proximal head 254, and a body 256. The proximal head 254 includes a central core portion 260 and a plurality of radially extending wings 262. In this example, the core portion 260 and the wings 262 form a rounded or blunt end to provide smooth insertion into the intramedullary canal.

The plurality of wings 262 extend radially from the core portion 260 and define the outer shape of the proximal head 254. In the embodiment shown, the proximal head 254, as measured from wing to wing, has a diameter sized to fit within an intramedullary canal of a phalanx and more particularly, within a canal of a proximal phalanx. In one aspect, the proximal head 254 has a maximum diameter of 2.5 mm, and the fixation device 250 has a length permitting it to be anchored within the subchondral bone while fusing a joint. In one aspect, the diameter of the proximal head 254 is in the range of about 1.5-3.0 mm. In another aspect, the diameter is within a range of about 2.0-2.5 mm. Various fixation device lengths may be provided to meet patient sizing requirements and to extend all the way to the base of the proximal phalanx to engage the subchondral bone. In one aspect, the length of the fixation device 250 in the range of about 19-80 mm. In another aspect, the length is in the range of about 23-40 mm. In yet another embodiment, the length is about 25 mm. Other lengths and ranges are contemplated.

Because of its rounded shape, the surgeon can feel tactilely when the fixation device is inserted to the depth of a bored or reamed hole because the rounded end resists further insertion at low insertion forces. However, the surgeon may still insert the fixation device into the intramedullary canal beyond the end of the bored or reamed area by applying additional force. Additional details of the fixation devices 100 and 250 can be found in U.S. Patent Application No. 61/780,360, filed on Mar. 13, 2013, titled "Hammertoe Implant with Enhanced Gripping Surfaces," incorporated herein by reference. Yet additional suitable fixation devices can be found in U.S. Patent Application No. 61/780,316, filed on Mar. 13, 2013, titled "Hammertoe Implant With Asymmetrical Head,", incorporated herein by reference.

Figure 7:
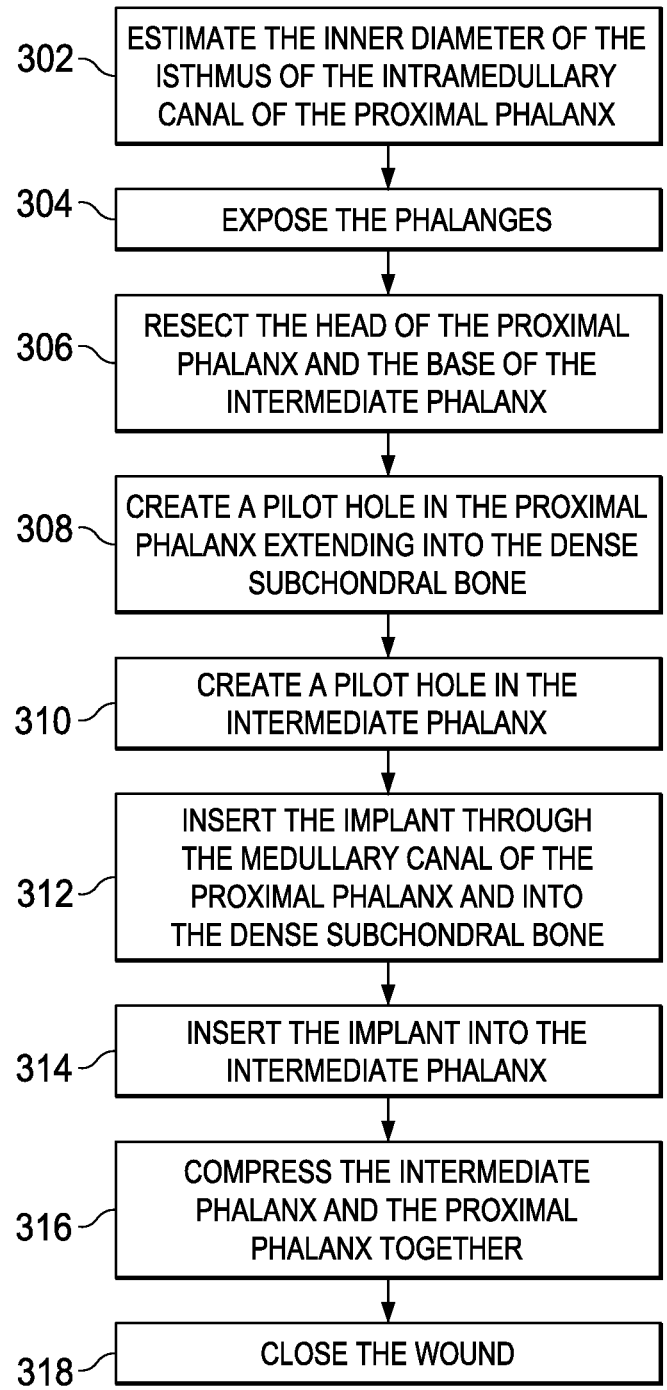
FIG. 7 is a flow chart showing an exemplary surgical technique in accordance with one aspect of the present disclosure.

FIG. 7 shows an exemplary operative technique 300 for implanting any of the devices described herein within a digit, such as a finger or toe of a patient. The technique will be described with reference to the fixation device 100, recognizing that the method also applies to any other fixation device described herein. The technique begins at a step 302 with the surgeon estimating the inner diameter of the isthmus of the intramedullary canal of the proximal phalanx 16. This may include examining pre-op radiographs to make the estimate. In some aspects, this may be done using a digital radiographs and a computer system configured to identify and estimate the size of the intramedullary canal. It may also include manual methods including measuring a radiograph with a ruler, taking into consideration radiographic magnification. The inner diameter of the isthmus of the intramedullary canal should be sized to permit the proximal head 104 of the fixation device 100 to pass through the narrowest point of the intramedullary canal in order to engage in the subchondral bone at the base of the proximal phalanx. Accordingly, when the proximal head 104 has a diameter of 2.5 mm, the surgeon may confirm that the narrowest location of the intramedullary canal is equal to or greater than 2.5 mm. The surgeon may also estimate the length of a suitable fixation device that will engage each phalanx at the intended location.

At a step 304, the surgeon exposes the proximal phalanx 16 and the intermediate phalanx 14. This may be done by creating an incision over the surgical digit, whether the digit is a finger or a toe. When the digit is a toe, the incision may be a standard 3 cm central incision in the toe in a manner known in the art. With the incision made, the surgeon may dissect through the skin and subcutaneous tissues down to the extensor tendon at the deep fascial level. In some techniques, this may include performing a transverse tenotomy/capsulotomy at the dorsal crown of the proximal phalanx. This may also include dissecting and transecting the medial and lateral collateral ligaments away from the bone to expose the head of the proximal phalanx into the surgical site. With the head of the proximal phalanx exposed, the surgeon may dissect soft tissue away from the base of the intermediate phalanx, exposing the cartilaginous surface for resection and arthrodesis preparation.

At a step 306, the surgeon resects the head of the proximal phalanx and the base of the intermediate phalanx. With the resections complete, the surgeon may then smooth all rough edges of bone.

At a step 308, the surgeon creates a pilot hole down the center of the intramedullary canal of the proximal phalanx with a reamer instrument. This step is shown in FIG. 8. FIG. 8 shows the proximal phalanx 16 and the intermediate phalanx 14 as resected in step 306, with a portion of a reamer instrument 350 reaming the intramedullary canal of the proximal phalanx 16. The reamer instrument 350 includes a cutter 352 and a driver 354. In this example, the cutter 352 has graduated etching that permits a surgeon to perceive the depth of the cutter 352. The surgeon may use fluoroscopy to ensure proper placement and depth of the cutter 352. In this method, the cutter 352 is advanced through the intramedullary canal, past the cancellous bone, and into the subchondral bone at the base of the proximal phalanx 16. This prepares the proximal phalanx 16 to receive a fixation device as described herein for anchoring in the subchondral to provide increased anchoring and support. In some instance, the depth of the cutter 352 may be measured with a depth gauge.

Figure 10:
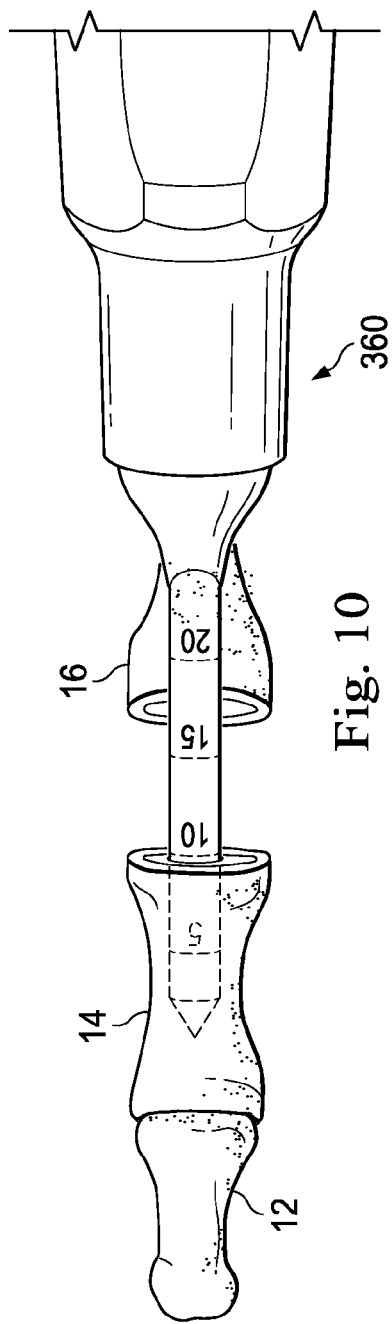
FIG. 10 is an illustration of phalanges undergoing a surgical technique in accordance with one aspect of the present disclosure.

At a step 310, the surgeon may then create a pilot hole down the center of the intramedullary canal of the intermediate phalanx 14 with the reamer instrument 350. This is shown in detail in FIG. 9, where the cutter 352 is shown introduced into the intermediate phalanx 14. In some embodiments, the pilot hole reaches to the subchondral bone of the intermediate phalanx 14. FIG. 10 shows a portion of a broach instrument 360 inserted into the pilot hole in the intermediate phalanx 14 to further prepare the pilot hole. The depth estimated during the pre-op planning should be taken into account. The surgeon may advance the broach instrument 360 until resistance is felt, usually between 7 mm to 10 mm into the intermediate phalanx 14. The insertion depth of the broach may be identified by the depth marking disposed on the broach instrument 360. In some embodiment, the surgeon may choose to not broach the proximal phalanx 16, while in other embodiments, the surgeon does broach the proximal phalanx 16.

Figure 11:
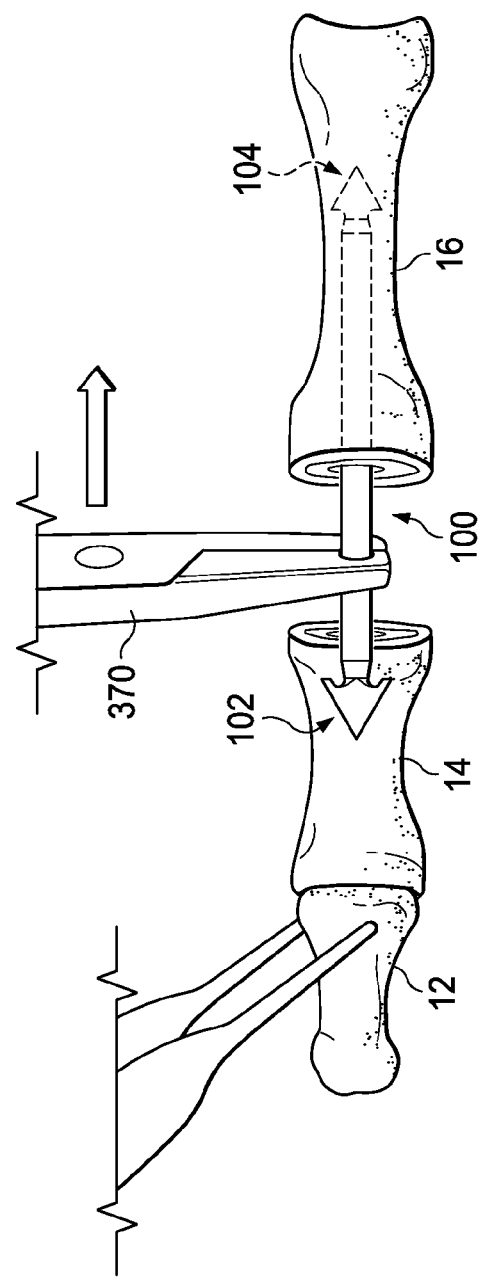
FIG. 11 is an illustration of phalanges undergoing a surgical technique in accordance with one aspect of the present disclosure.

At a step 312 in FIG. 7, the surgeon inserts the fixation device 100 into the prepared pilot holes in the proximal phalanx 16 so that it anchors in the dense subchondral bone. This step is shown in FIG. 11. The step may include grasping the fixation device 100 with insertion forceps 370. When the fixation device 100 has proximal and distal heads of different sizes, the surgeon may take care to insert the head with the smaller 2.5 mm proximal head. Since this technique results in a fixation device that extends further into the proximal phalanx 16 than the intermediate phalanx 14, the surgeon should grasp the fixation device 100 at a location distal of a middle region of the fixation device 100 with the insertion forceps 370. In some embodiments, more than 60% of the fixation device 100 extends into the proximal phalanx 16, and therefore, the surgeon grasps the fixation device 100 at location more than 60% of the fixation device's length from the proximal head 104. In other embodiments, more than 66% of the fixation device 100 extends into the proximal phalanx 16, and therefore, the surgeon grasps the fixation device at location more than 66% of the fixation device's length from the proximal head 104. In yet other embodiments, more than 70% of the fixation device extends into the proximal phalanx 16, and therefore, the surgeon grasps the fixation device at location more than 70% of the fixation device's length from the proximal head 104.

While properly grasping the fixation device 100 with the insertion forceps 370, the surgeon inserts an end of the device having a head diameter equal to or less than 2.5 mm (e.g., the proximal head 104) into the reamed pilot hole until the head 104 is engaged in the dense subchondral bone at the base of the proximal phalanx 16. This includes advancing the head 104 beyond the cancellous bone and penetrating the dense subchondral bone. This also may include advancing the head 104 until barbs, trailing edge surfaces, or other anchors on the proximal head 104 penetrate the subchondral bone. If the fixation device 100 seems caught and will not advance during the insertion process, the surgeon may remove the device, and trim one or both sides, edges, or wings of the proximal head 104 with a pin cutter to reduce the diameter. It is recommended to use fluoroscopy to confirm proper placement. FIG. 12 shows the device head 104 embedded within the dense subchondral bone of the proximal phalange.

Advancing the fixation device 100 is done by translating the device in an axial direction, without rotating the device. This may ensure that the remaining tissue about the pilot holes is intact and the proximal and distal heads have a minimal profile as they advance into the pilot hole. In some instances, if the proximal or distal heads becomes lodged, the surgeon may work the device gently side to side. However, any rotation should be limited, and is preferably not more than about 45 degrees.

At a step 314 in FIG. 7, the surgeon introduces the fixation device 100 into the intermediate phalanx 14. This may be accomplished by keeping the insertion forceps engaged on the fixation device 100, and grasping the digit and inserting the distal head 102 of the fixation device 100 into the entry portal prepared in the intermediate phalanx 14, as indicated in FIG. 12.

Figure 14:
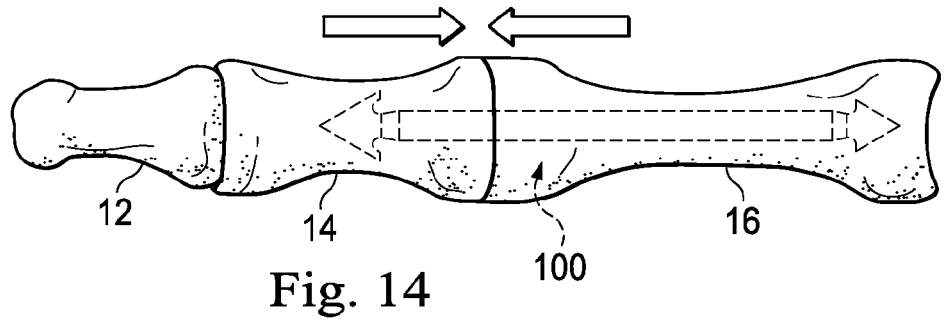
FIG. 14 is an illustration of phalanges undergoing a surgical technique in accordance with one aspect of the present disclosure.

FIG. 13 represents step 316 in FIG. 7. At step 316, the surgeon compresses the intermediate phalanx 14 and the proximal phalanx 16 until they both touch the insertion forceps 370. With the two bones advanced to abut the insertion forceps 370, the forceps are released and removed. As shown in FIG. 14, with the insertion forceps 370 removed, the surgeon further compresses the intermediate phalanx 14 and the proximal phalanx 16 against each other to advance the fixation device 100 both proximally and distally to its final and locked position. The final position of the fixation device 100 may be evaluated radiographically evaluate to ensure that the proximal and middle phalanges are in close contact. At a step 318, the surgeon closes the wound in accordance with generally accepted surgical technique.

Because the proximal head 104 is anchored within the dense subchondral bone, the device 100 has high pull-out strength relative to the small anchoring head size. Accordingly, the implanted fixation device 100 may have a lower incidence of migration due to external forces. In addition, because the anchoring site is so far spaced from the resection, the stability of the fixation device 100 is enhanced by the multiple points of contact along the intramedullary canal. While the technique was described with respect to the proximal and middle phalanges, the technique may also be used to implant a device in the intermediate phalanx 14 and the distal phalanx 12. In this type of procedure, the fixation device 100 is passed through the intramedullary canal of the intermediate phalanx 14 to anchor in the subchondral bone of the intermediate phalanx 14. In yet other techniques, the system is arranged so that pilot holes are created and the fixation device is configured to anchor in subchondral bone in the proximal phalanx, and also configured to anchor in subchondral bone in the intermediate phalanx. Using this technique, the pilot hole is formed in the intermediate phalanx to meet the subchondral bone and the distal head is introduced to the intermediate phalanx to anchor in the subchondral bone.

Figure 15:
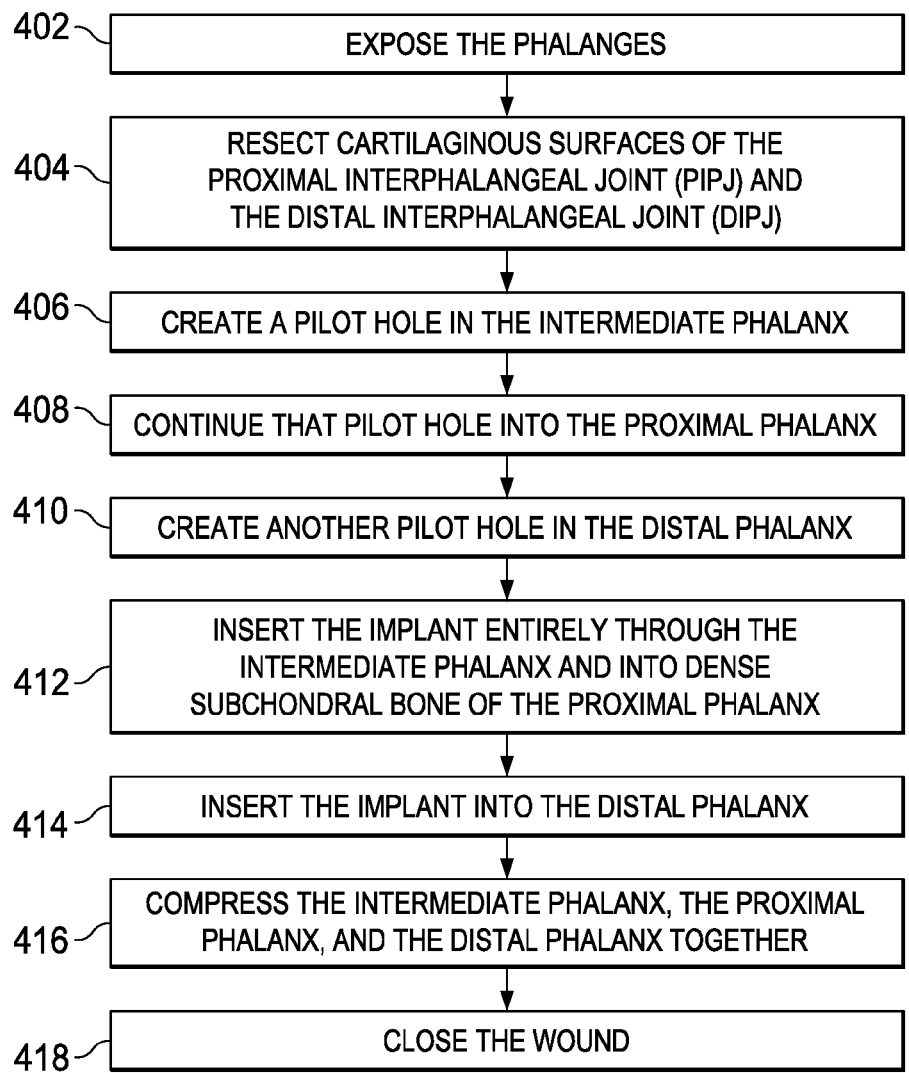
FIG. 15 is a flow chart showing an exemplary surgical technique in accordance with one aspect of the present disclosure.

FIG. 15 shows another exemplary operative technique 400 for implanting any of the devices described herein within a digit, such as a finger or toe of a patient. The technique 400 however includes implanting a device across two joints in the manner shown in FIG. 3. The technique 400 may have particular utility when both the PIPJ and DIPJ should be fused and the surgeon is concerned with having enough bone in the intermediate phalanx to use one fixation device for the PIPJ and another fixation device for the DIPJ. In some aspects, the multiple joint fusion described herein is accomplished by anchoring the proximal head of the fixation device 100 in the subchondral bone of the proximal phalanx 16. In addition, the surgery may be more efficient than implanting two separate devices, reducing hospital costs and fees. For the sake of efficiency, not all steps and nuances of each of the techniques are discussed with reference to both charts. However, it is understood that steps and description of one technique herein applies to other techniques herein.

The technique 400 may begin by estimating the inner diameters of the intermediate and proximal phalanges in the manner discussed above. A step 402 includes exposing the phalanges. This may be accomplished by first creating a linear incision from the metatarsophalangeal joint (MPJ) distally across the distal interphalangeal joint (DIPJ), thereby exposing the distal interphalangeal joint and the proximal interphalangeal joint (PIPJ). Disruption of the collateral ligaments around the joint spaces can be minimized. The surgeon may then transect the extensor tendons at the proximal interphalangeal joint (PIPJ) and reflect back to the MPJ. If the technique is used on the lesser digits, the MPJ may be released plantar with a McGlamry elevator to give a good range of motion at the MPJ and release any contracture in this area. The surgeon may then transect the extensor tendon at the DIPJ on the affected digit. Finally, the surgeon may transect the collateral ligaments at the PIPJ and DIPJ with care to leave as much collateral ligament to repair as possible.

At a step 404, the surgeon resects the cartilaginous surfaces from the PIPJ and DIPJ of the affected digit(s). When the technique is used to shorten a grossly elongated digit, the amount of bone needing to be removed should be distributed among all joint surfaces. This may include correcting the length of the overly elongated toe by removing bone from the proximal, middle, and distal phalanx to create a normal digital parabola, leaving enough bone in the distal phalanx to accommodate the 3.5 mm diameter distal head 102 of the fixation device 100. In some instances, the surgeon will remove the plantar fibrous plate of tissue covering the flexor tendons at the level of the joint. This may be necessary when the hammertoe contracture is severe or has been present for an extended period of time. If the plantar plate is thick and sponge-like, it can prevent achieving bone-on-bone contact of the phalanges. A sesamoid is often present at this level and, if problematic, should be removed as well.

At a step 406, the surgeon forms a pilot hole through the entire length of the intermediate phalanx 14. This may be accomplished using a reamer instrument, such as the reamer instrument 350 discussed above. The hole extends from the distal end of the intermediate phalanx 14 to the proximal end down the center of the intramedullary canal. Since the hole passes entirely through the length of the intermediate phalanx 14, a substantial amount of resistance is expected since the bone of the intermediate phalanx 14 may be very hard. To avoid accidental injury to the surgeon's hand, the intermediate phalanx may be held with an Alice clamp while placing the cutter 352 of the reamer instrument 350 through the intermediate phalanx. In some instances, fluoroscopy may be used to ensure proper placement of the reamer in the intermediate phalanx 14. Stop advancement of the cutter 352 when the tip protrudes from the proximal surface of the intermediate phalanx 14.

Figure 16:
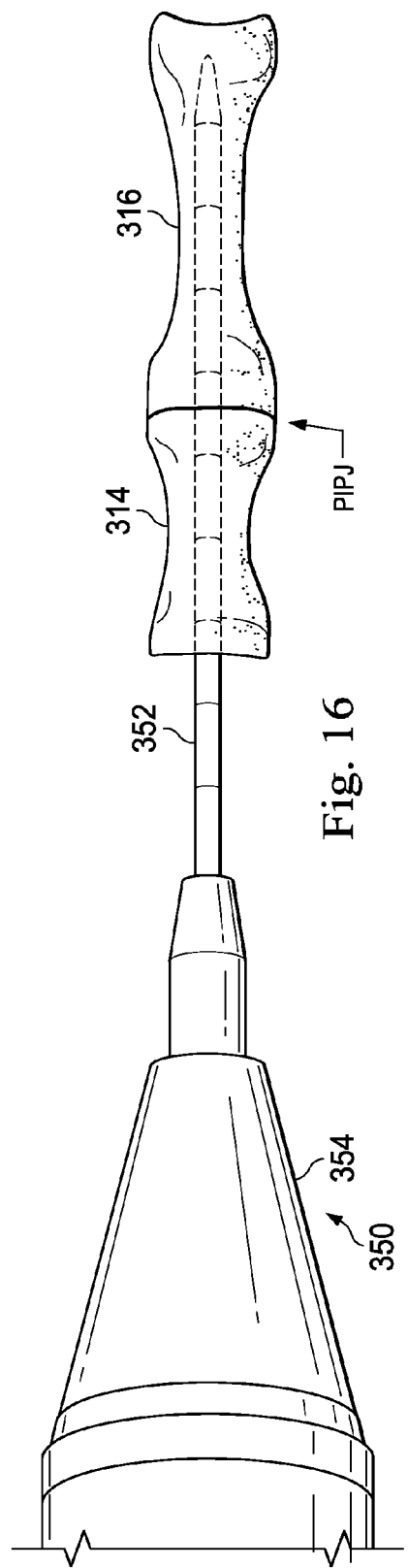
FIG. 16 is an illustration of phalanges undergoing a surgical technique in accordance with one aspect of the present disclosure.

With the hole formed in the intermediate phalanx 14, the surgeon may continue to form the pilot hole in the proximal phalanx 16 at step 408. In some instances, this includes forming the hole extending into the dense subchondral bone. FIG. 16 shows a reamer instrument 350 with a cutter 352 extending through the middle phalanx 14 and extending to the subchondral bone of the proximal phalanx 16. As can be seen, the reamer spans the PIPJ. Forming the hole may include grasping the proximal phalanx 16 and orienting the reamer tip protruding from the intermediate phalanx 14 so the reamer is aligned to create a pilot hole down the center of the proximal phalanx 16. Accordingly, the cutter 352 is advanced into the proximal phalanx 16 as it extends through the intermediate phalanx 14. The surgeon advances the cutter 352 until the tip is embedded in the subchondral bone at the base of the proximal phalanx 16 in the manner discussed above with reference to the method of FIG. 7. Accurate placement may be confirmed with fluoroscopy. Once proper placement is achieved, measure and note the precise depth of the reamer with a depth gauge.

At a step 410, the surgeon creates another pilot hole down the center of the intramedullary canal of the distal phalanx 12 with the reamer instrument 350. In some instances, the surgeon may review the lateral view while placing the reamer to confirm that the reamer cutter 352 has not pierced the nail bed. The pilot hole in the distal phalanx 12 may be prepared by broaching the hole with the broach 360 taking into account the depth estimated during pre-op planning Broach until resistance is felt, usually between 7 mm to 10 mm. Note the insertion depth of the broach as indicated by the depth marking.

At a step 412, the fixation device is introduced to the intermediate phalanx 14 and the into the dense subchondral bone of the proximal phalanx 16. This may include selecting a fixation device 100 that is appropriate considering the length as indicated by depth measurement taken when the reamer instrument was accurately placed in the intermediate and proximal phalanges 14, 16 plus the length reflected by the measurement taken from the depth of the broach in the distal phalanx 12. The fixation device 100 is then grasped with insertion forceps 370 at a location distal of the central region of the fixation device, as discussed above. Also as discussed above, the fixation device 100 should be oriented so the that proximal head 104 having a diameter of 2.5 mm or less can be inserted into through the intermediate phalanx 14 and into the proximal phalanx 16. In one aspect, the surgeon may grasp the distal head 102 of the fixation device 100 with the insertion forceps 370 so that the insertion force can be applied longitudinally behind the fixation device 100. Since the bone of the intermediate phalanx may be very hard, the intermediate phalanx may be held with an Alice clamp while passing the fixation device 100 from distal end to the proximal end through the intermediate phalanx.

The smaller proximal head 104 of the device 100 may be introduced into the reamed pilot hole in the intermediate phalanx 14. A small side-to-side motion while applying force may ease insertion of the fixation device 100 into the reamed pilot hole. When the tip of the proximal head 104 of the fixation device 100 protrudes from the proximal end of the intermediate phalanx 14, align the tip into the reamed pilot hole in the proximal phalanx 16.

The surgeon continues to advance the fixation device by pushing from the distal portion of the fixation device. After the fixation device has passed through the intermediate phalanx 14 and started into the proximal phalanx 16, the surgeon may take care to leave enough room between the middle and proximal phalanges to insert the insertion forceps and grasp the fixation device 100 prior to placing the distal head of the fixation device into the distal phalanx. This serves as a positive stop, preventing the fixation device 100 from inadvertently further advancing proximally rather than into the distal phalanx 12 during the distal phalanx insertion step. In some techniques however, the insertion forceps 370 engage the small space between the intermediate and distal phalanges 14, 12 during the press-fit of the distal head 102 into the distal phalanx 12.

The surgeon continues to advance the fixation device through the middle and proximal phalanges until the fixation device is engaged in the dense subchondral bone at the base of the proximal phalanx 16. The surgeon may use fluoroscopy to confirm proper placement. If the fixation device 100 seems caught and will not advance, one or both edges, sides, or wings of the proximal head 104 may be trimmed with a pin cutter to reduce the diameter.

At a step 414, the surgeon inserts the fixation device into the distal phalanx. In some instances, this includes releasing the fixation device 100 with the insertion forceps 370 and includes inserting the insertion forceps 370 between the intermediate and proximal phalanges 14, 16 to grip the fixation device 100 and prevent further movement in the proximal direction as the distal phalanx 12 is pressed onto the fixation device 100. With the fixation device 100 being held by the insertion forceps 370, the surgeon aligns the hole in the distal phalanx with the distal end of the fixation device and introduces the fixation device into the hole by sliding the distal phalanx 12 over the fixation device. When the distal head 102 has been press-fit into the distal phalanx, the clamp can be removed from the proximal space.

At a step 416, the surgeon grasps the distal and proximal phalanges and compresses them together so that the intermediate phalanx and the proximal phalanx abut one another and so that the intermediate phalanx and the distal phalanx abut one another. The surgeon may review the lateral view after fixation device placement to confirm that the fixation device has not broken through the bone and pierced the nail bed. The wound may then be cleaned, such as by flushing the wound with copious amounts of normal sterile saline. The surgeon may then reapproximate the collateral ligaments and the extensor tendons. At a step 418, the surgeon closes the subcutaneous tissue in layers and closes the skin in a conventional manner, resulting in multiple fused joints with the fixation device 100 as shown in FIG. 3.

The techniques disclosed herein employ a fixation device sized for passage deep along an intramedullary canal to anchor in the subchondral bone formed adjacent to the bases of the phalanges. This may provide a stronger pull-out resistance and may enable reduction of the overall diameter of the fixation device, while also providing additional support to the phalanx. In addition, fusing multiple joints with a single fixation device may increase the stability of the fixation device in the treated phalanges and provide continuity to the injured or deformed digit. Additional advantages are discussed herein.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A surgical method for bone fixation and stabilization on a patient, comprising:
    exposing at least a portion of a first base of afirst phalanx and a second phalanx at a joint of a patient;
    creating a passage in an intramedullary canal of the first phalanx extending through a first region of subchondral bone adjacent the first base, cancellous bone, and at least a portion of a second region of subchondral bone adjacent a second base of the first phalanx on an opposing side of the cancellous bone as compared to the first region of subchondral bone;
    inserting a first head portion of a fixation device along the passage in the intramedullary canal in a translating manner past the first region of subchondral bone and the cancellous bone in the first phalanx until the first head portion engages the second region of subchondral bone at the second base of the first phalanx, the fixation device having an opposing second head portion extending out of the passage from the first phalanx; and
    introducing the second phalanx onto the second head portion so that the second head portion anchors in cancellous bone of the second phalanx.

2. The surgical method of claim 1, further comprising inserting more than 60% of the fixation device into the intramedullary canal of the first phalanx.

3. The surgical method of claim 1, wherein the fixation device has a longitudinal length, and the method comprises grasping the fixation device with an insertion instrument at a location more than 60% of the longitudinal length from the first head portion in order to insert the first head portion along the passage and to engage the second region of subchondral bone.

4. The surgical method of claim 1, wherein inserting the first head portion in a translating manner includes rotating the fixation device less than about 45 degrees during insertion.

5. The surgical method of claim 1, wherein the first head portion comprises trailing edge surfaces configured to anchor in the second region of subchondral bone.

6. The surgical method of claim 1, wherein the first head portion has a diameter less than 2.5 mm.

7. The surgical method of claim 1, further comprising measuring the size of the intramedullary canal to ensure the first head portion can pass therethrough.

8. The surgical method of claim 1, further comprising intraoperatively trimming the first head portion to decrease its diameter when the first head portion is too large to pass through the intramedullary canal.

9. The surgical method of claim 1, wherein the first head portion has a smaller diameter than the second head portion.

10. The surgical method of claim 1, wherein the first head portion is a proximal head portion and the second head portion is distal head portion, and wherein the first phalanx is a proximal phalanx and the second phalanx is an intermediate phalanx.

11. The surgical method of claim 1, wherein introducing the second phalanx onto the second head portion includes advancing the second head portion such that the second head portion engages cortical bone of the second phalanx.

12. A surgical method for bone fixation and stabilization on a patient, comprising:
  exposing at least a portion of a first phalanx and a second phalanx at a joint of a patient, the first phalanx being more proximal than the second phalanx;
  creating a passage in an intramedullary canal of the first phalanx extending through a first region of subchondral bone adjacent the first base, cancellous bone, and into at least a portion of a second region of subchondral bone adjacent a second base of the first phalanx on an opposing side of the cancellous bone as compared to the first region of subchondral bone;
  inserting more than 60% of a fixation device into the passage in the intramedullary canal past the first region of subchondral bone and the cancellous bone in the phalanx until a first head portion of the fixation device engages the second region of subchondral bone at the second base of the first phalanx, the fixation device having an opposing second head portion extending out of the passage from the first phalanx; and
  introducing the second phalanx onto the second head portion so that the second head portion anchors in cancellous bone of the second phalanx.

13. The surgical method of claim 12, wherein inserting comprises translating the fixation device along the passage so that the device rotates less than about 45 degrees while inserting.

14. The surgical method of claim 12, wherein the fixation device has a longitudinal length, and the method comprises grasping the fixation device with an insertion instrument at a location more than 60% of the longitudinal length from the first head portion in order to insert more than 60% of the fixation device into the first phalanx to engage the second region of subchondral bone.

15. The surgical method of claim 12, wherein the first head portion comprises trailing edge surfaces configured to anchor in the second region of subchondral bone.

16. The surgical method of claim 12, wherein the first head portion has a diameter less than 2.5 mm.

17. The surgical method of claim 12, further comprising measuring the size of the intramedullary canal to ensure the first head portion can pass therethrough.

18. A surgical method for bone fixation and stabilization on a patient, comprising:
  exposing a proximal interphalangeal joint (PIPJ) joining a proximal phalanx and an intermediate phalanx, and a distal interphalangeal joint (DIPJ) joining the intermediate phalanx and a distal phalanx;
  creating a hole entirely through the intermediate phalanx;
  creating a hole into the proximal phalanx extending through a first region of subchondral bone adjacent a first base of the proximal phalanx adjacent to the PIPJ, cancellous bone, and at least a portion of a second region of subchondral bone adjacent a second base of the proximal phalanx on an opposing side of the cancellous bone as compared to the first region of subchondral bone;
  inserting a first head portion of a fixation device through the hole in the intermediate phalanx and into the hole in the proximal phalanx past the first region of subchondral bone and the cancellous bone so that the first head portion engages the second region of subchondral bone at the second base and an opposing second head portion of the fixation device extends out of the passage from the intermediate phalanx; and
  introducing the distal phalanx onto the second head portion so that the second head portion anchors in cancellous bone of the distal phalanx.

19. The surgical method of claim 18, further comprising inserting more than 60% of the fixation device into the intramedullary canal of the intermediate and proximal phalanges.

20. The surgical method of claim 18, wherein the fixation device has a longitudinal length, and the method comprises grasping the fixation device with an insertion instrument at a location more than 60% of the longitudinal length from the first head portion in order to insert the first head portion along the passage and engage the second region of subchondral bone of the proximal phalanx.

21. The surgical method of claim 18, wherein inserting the first head portion includes advancing the head portion in a translating manner.

22. The surgical method of claim 21, wherein the translating manner includes rotating the device within the hole in less than about 45 degrees while advancing the head portion.

23. The surgical method of claim 18, wherein the first head portion has a diameter less than 2.5 mm.

24. The surgical method of claim 18, further comprising measuring the size of the intramedullary canal of the intermediate and proximal phalanges to ensure the first head portion can pass therethrough.

25. The surgical method of claim 18, wherein the first head portion has a smaller diameter than the second head portion.

26. The surgical method of claim 18, comprising grasping the fixation device with a surgical instrument between the proximal phalanx and the intermediate phalanx while introducing the distal phalanx onto the second head portion.

27. The surgical method of claim 18, wherein introducing the second phalanx onto the second head portion includes advancing the second head portion in the second phalanx until the second head portion engages cortical bone of the second phalanx.

28. A surgical method for bone fixation and stabilization on a patient, comprising:

exposing a proximal interphalangeal joint (PIPJ) joining a first phalanx and a second phalanx, and a distal interphalangeal joint (DIPJ) joining the second phalanx and a third phalanx;

inserting a first head portion of a fixation device entirely through the second phalanx and into the first phalanx through a first region of subchondral bone adjacent a first base of the first phalanx adjacent to the PIPJ, cancellous bone, and at least a portion of a second region of subchondral bone adjacent a second base of the first phalanx on an opposing side of the cancellous bone as compared to the first region of subchondral bone until the first head portion engages the second region of subchondral bone at the second base of the first phalanx, and so that an opposing second head portion of the fixation device extends out from the second phalanx; and introducing the third phalanx onto the second head portion so that the second head portion anchors in cancellous bone of the third phalanx.

29. The surgical method of claim 28, comprising:

forming a pilot hole from the DIPJ entirely through the second phalanx;

forming a pilot hole from the DIPJ through the first region of subchondral bone and cancellous bone of the first phalanx until the pilot hole reaches the second region of subchondral bone; and forming a pilot hole from the DIPJ through a portion of the third phalanx.

30. The surgical method of claim 28, wherein inserting the first head portion includes advancing the head portion in a translating manner.

31. The surgical method of claim 28, wherein the translating manner includes rotating the device within the hole in less than about 45 degrees during insertion.

32. The surgical method of claim 28, wherein the first head portion has a diameter less than 2.5 mm.

* * * * *

UNITED STATES PATENT AND TRADEMARK OFFICE
CERTIFICATE OF CORRECTION

PATENT NO. : 9,717,543 B2  
APPLICATION NO. : 14/206281  
DATED : August 1, 2017  
INVENTOR(S) : Brown et al.

Page 1 of 1

It is certified that error appears in the above-identified patent and that said Letters Patent is hereby corrected as shown below:

In the Claims

Column 16, Line 38: Claim 1, Delete "afirst" and insert -- a first --

Column 17, Line 28: Claim 11, Delete "portion engages cortical bone" and insert -- portion is further anchored in cortical bone --

Column 18, Line 27: Claim 27, Delete "portion engages cortical bone" and insert -- portion is further anchored in cortical bone --

Signed and Sealed this
Third Day of October, 2017

Joseph Matal
*Performing the Functions and Duties of the*
*Under Secretary of Commerce for Intellectual Property and*
*Director of the United States Patent and Trademark Office*